United States Patent
Lehmann et al.

(10) Patent No.: US 7,416,857 B2
(45) Date of Patent: Aug. 26, 2008

(54) DIFFERENTIAL DIAGNOSIS WITH HEPCIDIN

(75) Inventors: Paul Lehmann, Worms (DE); Ralf Roeddiger, Gorxheimertal (DE)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 10/972,101

(22) Filed: Oct. 22, 2004

(65) Prior Publication Data

US 2005/0148025 A1 Jul. 7, 2005

(30) Foreign Application Priority Data

Oct. 22, 2003 (DE) .................... 103 49 124

(51) Int. Cl.
*C12Q 1/37* (2006.01)
(52) U.S. Cl. ....................................... 435/23
(58) Field of Classification Search ............... None
See application file for complete search history.

(56) References Cited

FOREIGN PATENT DOCUMENTS

| | | |
|---|---|---|
| WO | WO 98/04248 | 2/1998 |
| WO | WO 02/098444 | 12/2002 |
| WO | WO 03/025583 | 3/2003 |
| WO | WO 2004/058044 A | 7/2004 |

OTHER PUBLICATIONS

American Heart Association website, "Inflammation, Heart Disease and Stroke: The Role of C-Reactive Protein," www.americanheart.org/presenter.jhtml?identifier=4648, Available Online: Jun. 5, 2003.*
Centenary Cardiology website, "Homocysteine," www.centenarycardiology.com/Conditions/Homocysteine.htm, Available Online: Dec. 27, 2002.*
Sowers et al, "C-reactive Protein as a biomarker of emergent osteoarthritis," (Osteoarthritis and Cartilage), vol. 10, pp. 595-601.*
Dallalio et al, "Serum hepcidin in clinical specimens," (British Journal of Haematology), 2003, vol. 122, pp. 996-1000.*
Nemeth Elizabeta et al., 2003, "Hepcidin, a putative mediator of anemia of inflammation, is a type II acute-phase protein", Blood vol. 101(7).
Nicolas Gael et al., 2002, "The gene encoding the iron regulatory peptide hepcidin is regulated by anemia, hypoxia, and inflammation", The Journal of Clin. Invest. vol. 110(7).
Weinstein David A et al., 2002, "Inappropriate expression of hepcidin is associated with iron refractory anemia: implications for the anemia of chronic disease", Blood vol. 100(10).
Roetto Antonella et al., 2003, "Mutant antimicrobial peptide hepcidin is associated with sever juvenile hemochromatosis", Nature Genetics, vol. 33(1).
Okka Mehmet et al., 2002, "Plasma homocysteine level and uveitis in Behcet's disease", The Israel Medical Assoc. J, vol. 4(11).
Theuma P et al., 2003, "Inflammation and emerging risk factors in diabetes mellitus and atherosclerosis", Curr. Diab. Reports, vol. 3(3).
Park et al., 2001, "Hepcidin, a urinary antimicrobial peptide synthesized in the liver", J. Biol. Chem., vol. 276(11).
Nicolas et al., 2002, "Hepcidin, a new iron regulatory peptide", Blood cells, Molecules and Diseases, vol. 29(3).
Weiss G et al., 1997, "Pathways for the regulation of macrophage iron metabolism by the anti-inflammatory cytokines IL-4 and IL-3", J. Immunology, vol. 158(1).
T. Bjerregaard Larsen, et al., (2002) "Hyperhomocysteinaemia, Coagulation Pathway Activation and Thrombophilia in Patients with Inflammatory Bowel Disease", Taylor & Francis Healthsciences, Scand J. Gastroenterol (1), pp. 1-6.
I. Morgenstern, et al., (2003), "Homocysteine, Cysteine, and Glutathione in Human Colonic Mucosa", Digestive Diseases and Sciences, vol. 48(10), pp. 2083-2090.

\* cited by examiner

*Primary Examiner*—Ralph Gitomer
*Assistant Examiner*—Amanda P Wood
(74) *Attorney, Agent, or Firm*—McDonnell Boehnen Hulbert & Berghoff LLP

(57) ABSTRACT

The present invention concerns the use of hepcidin as a marker for detecting inflammatory chronic diseases and especially for a differential diagnosis to detect inflammatory chronic diseases and/or non-inflammatory chronic diseases. The present invention also concerns a method for detecting inflammatory chronic diseases, non-inflammatory chronic diseases and/or acute phase reactions comprising the determination of hepcidin.

10 Claims, 3 Drawing Sheets

DIFFERENTIAL DIAGNOSIS WITH HEPCIDIN

CROSS REFERENCE

This application claims priority to German patent application no. DE 103 49 124.4 filed Oct. 22, 2003, which is incorporated by reference herein in its entirety.

BACKGROUND OF THE INVENTION

Chronic diseases are widespread and include numerous inflammatory and non-inflammatory diseases of a wide variety of organs. Chronic diseases often considerably limit the quality of life of the affected patients. Hence it is desirable to provide more rapid and reliable diagnostic methods in order to optimize the treatment and care of patients with chronic diseases.

Certain physiological parameters such as gammaglobulins, blood sugar level, or other blood values are often determined in order to diagnose diseases. However, it is difficult to distinguish between or determine non-inflammatory chronic diseases, inflammatory chronic diseases and/or acute phase reactions. There are still no specific markers for many chronic diseases. For example general inflammatory markers are used in the prior art to diagnose chronic inflammatory diseases. However, a problem with this is that many of these parameters are not only increased or changed in a patient with a chronic inflammation but also in an acute phase reaction such as an infection or injury.

Thus there is a major need for new markers that are suitable for the diagnostic problems in connection with chronic diseases. In particular there is a need for markers which enable a differentiation between non-inflammatory chronic diseases, inflammatory chronic diseases and/or acute phase reactions.

SUMMARY OF THE INVENTION

The present invention concerns the use of hepcidin as a marker for detecting inflammatory chronic diseases and especially for a differential diagnosis to detect inflammatory chronic diseases and/or non-inflammatory chronic diseases. The present invention also concerns a method for detecting inflammatory chronic diseases, non-inflammatory chronic diseases and/or acute phase reactions comprising the determination of hepcidin.

DETAILED DESCRIPTION OF THE INVENTION

Figure 1:
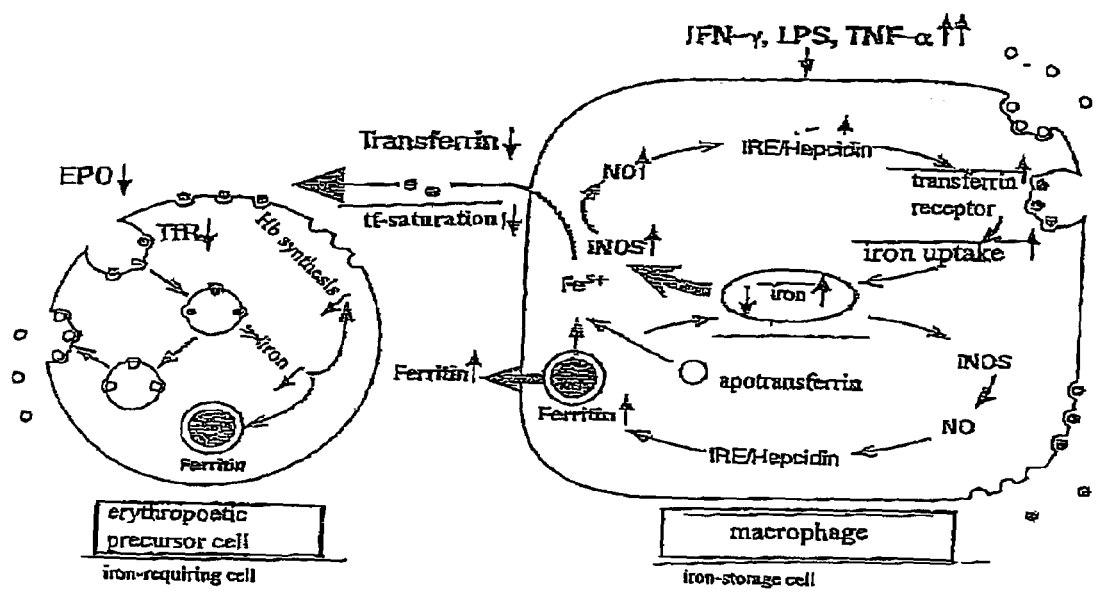
FIG. 1 shows a model of the autoregulation of iron metabolism and the NO/NOS cycle in activated monocytes/macrophages and the supply of a cell requiring iron (Weiβ, G. et al., 1997).

It is now surprisingly found that hepcidin can be used as a marker to detect inflammatory chronic diseases and also in differential diagnosis to distinguish inflammatory chronic diseases and/or non-inflammatory chronic diseases.

Hepcidin is a peptide consisting of 20 (SEQ ID NO:1), 22 (SEQ ID NO:2) or 25 (SEQ ID NO:3) amino acids (Park et al., J. Biol. Chem. Vol. 276, No. 11, p. 7806-7810, 2001) which are cleaved from hepcidinogen. Hepcidin is produced in the liver and plays an essential role in iron metabolism (Nicolas et al., Blood cells, Molecules and Diseases (2002) 29(3): 327-335).

It is currently assumed that hepcidin regulates the release of iron from macrophages to the erythropoietic precursor cells; an increased hepcidin level inhibiting iron release. In macrophages, high iron concentration increases inducible nitric oxide synthetase. This induces cytokine production, which in turn can trigger chronic inflammation.

Thus it is advantageously possible to diagnose chronic diseases which are for example characterized by a functional iron deficiency, haemochromatoses, diabetes, rheumatoid arthritis, arteriosclerosis, tumors or kidney failure with the aid of the marker hepcidin.

Hepcidin can, for example, be determined from serum, plasma or urine. It is preferably determined from serum. The reference values for the measured variable hepcidin are for example in the range of about 0 to 1000 ng/ml, in particular 100 to 500 ng/ml. A particularly preferred reference range is about 200 to 260 ng/ml. Any value within the reference range can be used as a threshold value for the measurement, for example a value in the range of 0 to 1000 ng/ml. A value between 100 and 500 ng/ml is preferably used as a threshold value.

The determination of hepcidin can be effected, for example, by means of the Hepcidin Prohormone ELISA test available from DRG, located in Marburg, Germany.

Particularly good and reliable diagnosis is possible when one or more markers are used in addition to hepcidin. Markers are preferably determined which are suitable for detecting inflammatory chronic diseases and/or non-inflammatory chronic diseases. Preferred markers are for example acute phase proteins, regulators of the synthesis of acute phase proteins, homocysteine, hs-CRP, SAA, C-reactive protein (CRP), serum amyloid A (SAA), $\alpha_1$-antichymotrypsin, acidic $\alpha_1$ glycoprotein, $\alpha_1$ antitrypsin, haptoglobin, fibrinogen, complement component C3, complement component C4, coeruloplasmin, interleukin 6 (IL-6), leukemia-inhibiting factor (LIF), oncostatin M, interleukin 11 (IL-11), ciliary neurotropic factor (CNTF), interleukin 1α (IL-1α), interleukin 1β (IL-1β), tumor necrosis factor α(TNFα), tumor necrosis factor β (TNFβ), insulin, fibroblast growth factor (FGF; fibroblast growth factor), hepatocyte growth factor, transforming growth factor β (TGFβ) and/or interferon. Moreover, it is also possible to use other markers that are used in the special field.

The use of one or more markers in addition to hepcidin can ensure a more accurate and reliable diagnosis of a disease. As a result the psychic and physical stress of the affected patients can be reduced or eliminated even more rapidly by specific therapeutic measures. The use of several markers is especially advantageous when one or more other diseases are present in a patient in addition to a chronic disease.

In some diagnostic problems it is particularly desirable to differentiate between the presence of a non-inflammatory chronic disease and/or inflammatory chronic disease. It was surprisingly now found that this is possible by determining the markers hepcidin and homocysteine.

Thus in an advantageous embodiment the present invention concerns a method for detecting chronic diseases comprising the determination of
(i) hepcidin and
(ii) homocysteine.

The method according to the invention can for example be used to detect inflammatory and/or non-inflammatory chronic diseases. In particular the detection of hepcidin and homocysteine advantageously enables a distinction to be made between the presence of a non-inflammatory chronic disease and/or an inflammatory chronic disease or an unequivocal classification as a non-inflammatory and/or inflammatory chronic disease. In this connection, an increased hepcidin content indicates the presence of an inflammatory chronic disease whereas an increased homocysteine content indicates a non-inflammatory chronic disease.

Inflammatory chronic diseases which can be detected by the method according to the invention are for example haematochromatoses, diabetes, rheumatoid arthritis and other rheumatoid diseases, arteriosclerosis, vasculitis, tumors, kidney failure and systemic lupus erythematosus. Non-inflammatory chronic diseases which can be detected by the method according to the invention are for example vitamin deficiencies, in particular B6, B12 and folate deficiencies, pellagra, funicular myelosis, pseudoencephalitis, hemodegenerative diseases such as Alzheimer's and vascular diseases e.g. coronary heart disease and peripheral occlusive arterial disease.

The determination of hepcidin and the threshold values are as described above.

Homocysteine can for example be determined from serum, plasma or urine. It is preferably determined from serum. The reference values for the measured variable homocysteine are preferably in the range of about 3 to 18 µmol/l, preferably about 5 to 15 µmol/l, in particular about 15 µmol/l. Any value within the reference range can be used for the measurement as a threshold value, for example 12, 13, 14 or 15 µmol/l. 15 µmol/l is preferably used as the threshold value.

In this embodiment of the method according to the invention a classification into the following groups is preferably carried out:
a) no chronic disease,
b) inflammatory chronic disease,
c) non-inflammatory chronic disease, and
d) inflammatory chronic disease as well as non-inflammatory chronic disease.

The following diagram illustrates a classification model based on the determination of hepcidin and homocysteine.

inflammatory chronic diseases and/or temporary acute phase reactions which often have similar symptoms. The use of general inflammatory markers is usually unsatisfactory in such cases since these are increased or changed in temporary acute phase reactions as well as in chronic inflammatory diseases. It was now found that by determining hepcidin and an acute phase protein and/or a regulator of the synthesis of acute phase proteins, it is possible to differentiate between inflammatory chronic diseases and temporary acute phase reactions.

An advantageous embodiment of the present invention thus concerns a method for detecting inflammatory chronic diseases and/or acute phase reactions comprising the determination of:
(i) hepcidin and
(iii) an acute phase protein and/or a regulator of the synthesis of acute phase proteins.

Examples of acute phase proteins which can be determined in the method according to the invention are for example C-reactive protein (CRP), serum amyloid A (SAA), α1-antichymotrypsin, acidic α1-glycoprotein, α1-antitrypsin, haptoglobin, fibrinogen, complement component C3, complement component C4 and/or coeruloplasmin. Examples of regulators for the synthesis of acute phase proteins are for example interleukin 6, leukemia inhibitor factor (LEF), oncostatin M, interleukin 11, ciliary neurotropic factor (CNTF), interleukin 1 (IL-1), interleukin 1β (IL-1β), tumor necrosis factor α (TNF α), tumor necrosis factor β (TNF β), insulin, fibroblast growth factor, hepatocyte growth factor, transforming growth factor β (TGF β) and/or interferon. CRP, SAA, IL6, IL1 and/or TNF α are preferably determined. C-reactive protein is particularly preferably determined in the method according to the invention as the acute phase protein.

The reference values and methods for determining hepcidin are as described above.

Suitable reference values for the measured variable C-reactive protein are for example in the range of 7 to 13 mg/l, preferably about 8 to 12 mg/l, particularly preferably about 9 to 11 mg/l and in particular about 10 mg/l. Any value within

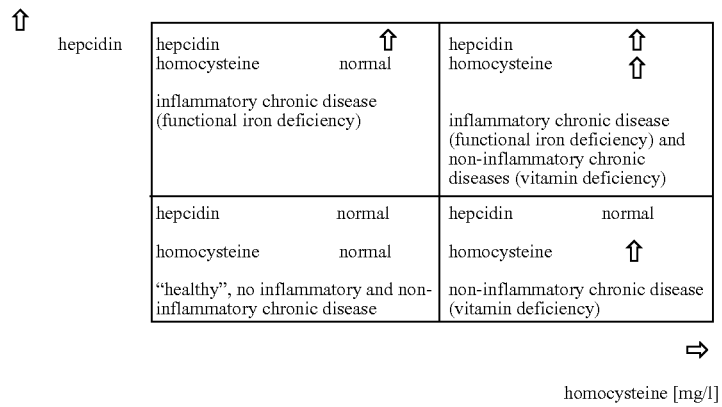

the reference range can be used for the measurement as a threshold value for example 9, 10, or 11 mg/l. 10 mg/l is preferably used as the threshold value.

In this embodiment of the method according to the invention a classification into the following groups is preferably carried out:

Also in this embodiment of the method according to the invention it is possible to additionally use one or more markers in addition to hepcidin and homocysteine. Suitable markers are listed above.

In the clinical routine problems often occur where it is desirable to diagnose or differentiate between the presence of a) no acute phase reaction, no inflammatory chronic disease,
b) inflammatory chronic disease with acute phase reaction and
c) acute phase reaction, no inflammatory chronic disease and
d) inflammatory chronic disease, no acute phase reaction.

The determination of hepcidin and an acute phase protein and/or a regulator of the synthesis of acute phase proteins advantageously enable a differentiation between the presence of an inflammatory chronic disease and/or a temporary acute phase reaction. In this case an increased hepcidin content indicates the presence of an inflammatory chronic disease, an increased content of an acute phase protein and/or a regulator of the synthesis of acute phase proteins indicates the presence of a temporary acute phase reaction.

The following diagram illustrates a classification model based on the determination of hepcidin and C-reactive protein (CRP).

in the other embodiments of the method according to the invention and are described above.

In this embodiment it is advantageously possible to diagnose inflammatory chronic diseases, temporary acute phase reactions and/or non-inflammatory chronic diseases. In this embodiment a classification is preferably made into the following groups:
a) neither non-inflammatory nor inflammatory chronic disease, no acute phase reaction,
b) non-inflammatory chronic disease (no inflammatory chronic disease, no acute phase reaction),
c) inflammatory chronic disease and acute phase reaction, (no non-inflammatory chronic disease),
d) inflammatory chronic disease (no acute phase reaction, no non-inflammatory chronic disease),
e) non-inflammatory chronic disease and acute phase reaction, (no inflammatory chronic disease),
f) acute phase reaction (neither non-inflammatory nor inflammatory chronic disease),

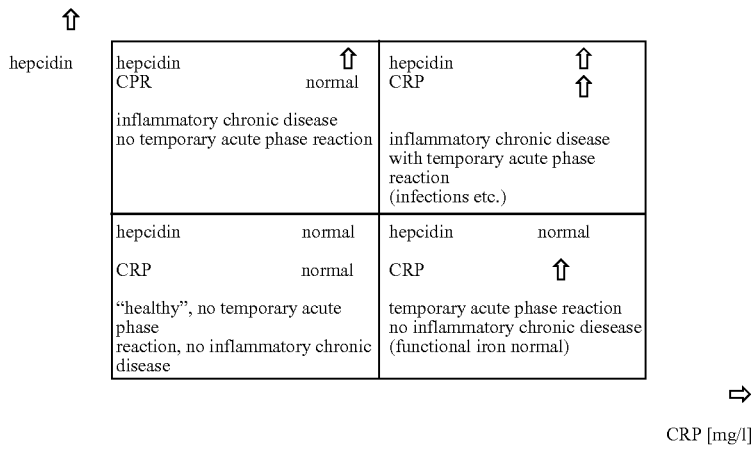

With regard to the combination of an elevated hepcidin content and a normal CRP value shown in the figure it should be noted that the occurrence of such a combination is basically possible but very improbable.

Also in this embodiment of the method according to the invention it is possible to additionally use one or more markers in addition to hepcidin and an acute phase protein and/or a regulator of the synthesis of acute phase proteins. Suitable markers are listed above.

When diagnosing patients, cases often occur in which it is necessary to differentiate between inflammatory chronic diseases and non-inflammatory chronic diseases as well as between inflammatory chronic diseases and acute phase reactions. This is advantageously possible by determining the parameters hepcidin, homocysteine and an acute phase protein and/or a regulator of the synthesis of acute phase proteins.

In a particularly preferred embodiment of the method according to the invention the following are hence determined:
(i) hepcidin,
(ii) homocysteine; and
(iii) an acute phase protein and/or a regulator of the synthesis of acute phase proteins.

The reference values of the parameters determined in this embodiment correspond to those which have been described g) non-inflammatory chronic disease and inflammatory chronic disease and acute phase reaction, and
h) non-inflammatory chronic disease and inflammatory chronic disease (no acute phase reaction).

A patient who is classified into group a) has neither a chronic disease nor an acute phase reaction and requires no further treatment.

A patient who is classified into group b) on the basis of the determined values for the markers i), ii) and iii) suffers from a non-inflammatory chronic disease. An inflammatory chronic disease or an acute phase reaction is not present. Possible diseases which come into consideration are for example B vitamin deficiency diseases of the nervous system such as funicular myelosis or pseudoencephalitis, pellagra, neurodegenerative diseases such as for example Alzheimer's disease or vascular diseases such as coronary heart disease or arterial diseases.

A patient who is classified into group c) suffers from an inflammatory chronic disease and has an acute phase reaction. A non-inflammatory chronic disease is not present in this patient. Possible diseases which come into consideration are for example pancreatitis, hepatitis, rheumatoid diseases, systemic lupus erythematosus and vasculitis.

A patient who is classified into group d) has an inflammatory chronic disease. An acute phase reaction or a non-inflammatory chronic disease is not present. Possible diseases which come into consideration are for example chronic anemia and tumor diseases.

A patient who is classified into group e) has a non-inflammatory chronic disease and an acute phase reaction. An inflammatory chronic disease is not present.

A patient who is classified into group f) has neither a non-inflammatory chronic disease nor an inflammatory chronic disease. The patient only has an acute phase reaction.

A patient who is classified into group g) has a non-inflammatory chronic disease as well as an inflammatory chronic disease and an acute phase reaction.

A patient who is classified into group h) has a non-inflammatory chronic disease as well as an inflammatory chronic disease, however, no acute phase reaction is present.

In all embodiments of the method according to the invention one or more markers can be determined in addition to the said parameters. The following are for example preferably determined: holotranscobalamin II, methylmalonic acid, cystathionine, acute phase proteins, regulators of the synthesis of acute phase proteins, transferrin, soluble transferrin receptor (sTfR), ferritin, creatinine, hemoglobin, blood glucose, triglycerides, cholesterol, zinc, protoporphyrin, myoglobin, haemosiderin, catalase, peroxidase and cytochrome. Moreover, other markers used in the special field can also be used. A combination of the markers according to the invention with other markers advantageously enables a very wide spectrum of diverse diseases to be identified in one diagnostic step.

The method according to the invention also advantageously enables a differential diagnosis. The aim of a differential diagnosis is to distinguish between and identify one or more particular diseases within a group of diseases that have similar or even in some cases identical symptoms. Surprisingly the method according to the invention enables a distinction or identification of inflammatory chronic diseases, non-inflammatory chronic diseases and acute phase reactions which often have very similar symptoms.

Furthermore, the method according to the invention can be used in combination with other diagnostic methods or methods of differential diagnosis. For example a combination of the method according to the invention with a test for determining disorders of iron metabolism and/or vitamin disorders is particularly preferred. In this case disorders of vitamin B6, vitamin B12 and folic acid balance are preferably determined. This not only allows the disease itself but also in many cases the cause of the disease such as a vitamin deficiency to be advantageously determined in one diagnostic step.

Figure 2:
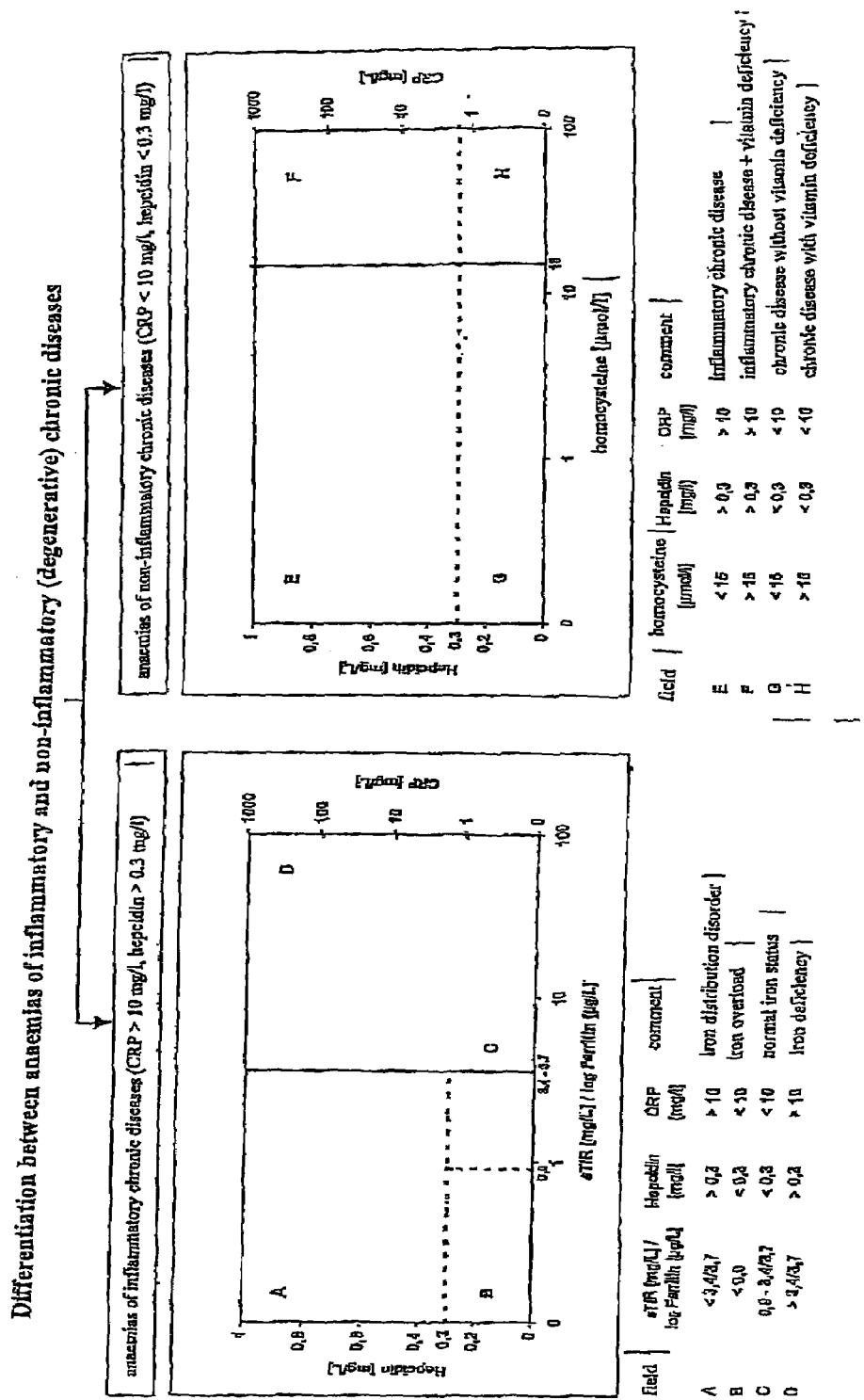
FIG. 2 shows a schematic representation of the differentiation between anemia in inflammatory and non-inflammatory chronic diseases.
Figure 3:
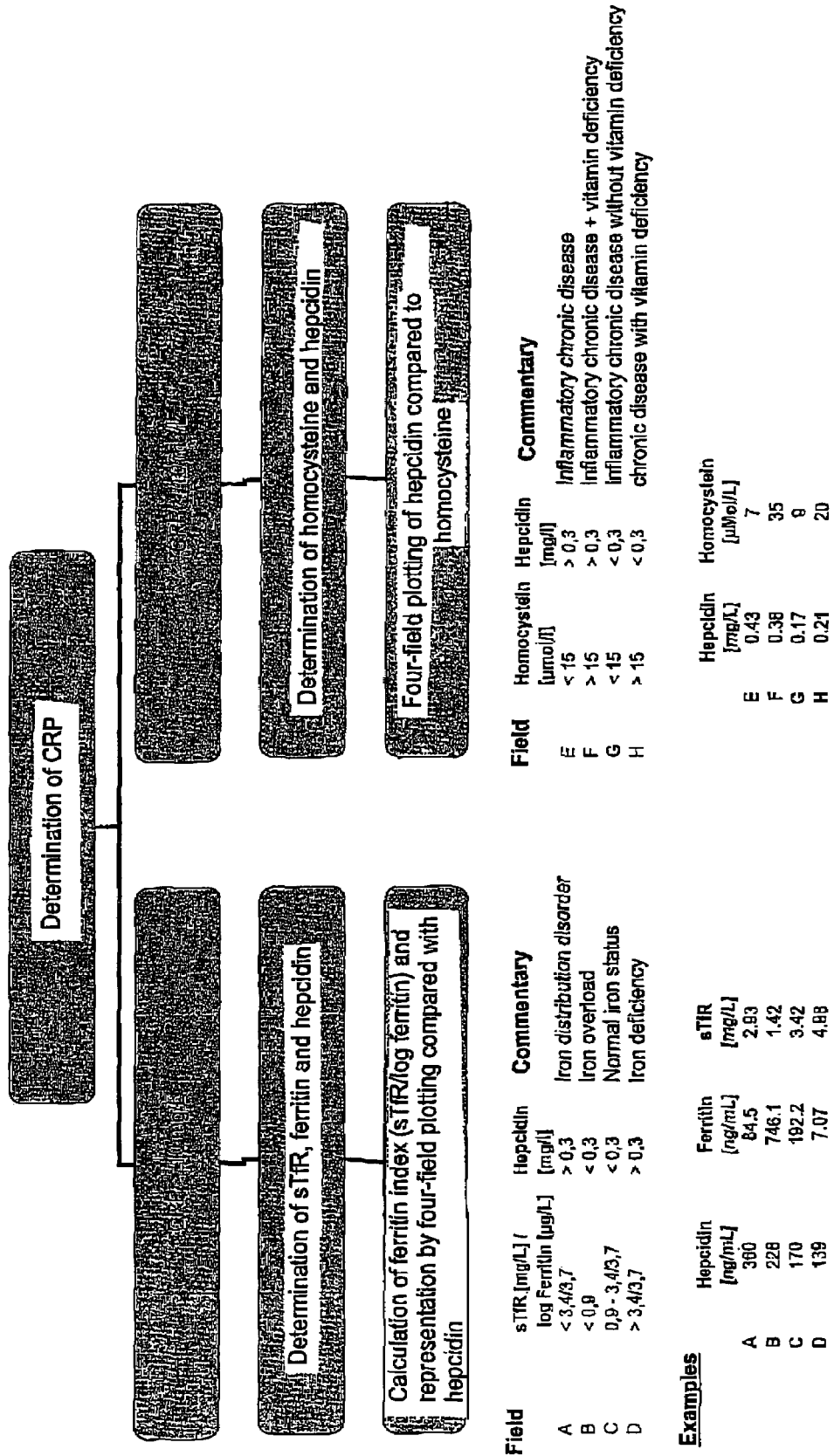
FIG. 3 shows values obtained in the study described in Example 1.

The present invention is further illustrated by FIGS. 1 to 3.

FIG. 1 shows a model of the autoregulation of iron metabolism and the NO/NOS cycle in activated monocytes/macrophages and the supply of a cell requiring iron (Weiβ, G. et al., 1997). The abbreviations in FIG. 1 are as follows: IFN-γ: interferon γ, iNOS: induced nitric oxide synthase, IRE: iron reacting element, IRE/hepcidin: high-affinity binding of hepcidin to IRES, LPS: lipopolysaccharide, TNFα: tumor necrosis factor α, |and| indicate an increase or decrease of cellular reactions in the supply of an iron-requiring cell. FIG. 1 shows that transferrin synthesis is suppressed and transferrin saturation is lowered by an upregulation of hepcidin. In macrophages a high iron concentration results in an increase in induced nitric oxide synthetase (iNOS). This induces cytokine production which can trigger chronic diseases.

FIG. 2 shows a schematic representation of the differentiation between anemia in inflammatory and non-inflammatory chronic diseases.

FIG. 3 shows a differential diagnostic procedure using different markers, e.g. CRP, sTfR, ferritin, hepcidin, and homocysteine. Examples A to H illustrate various conditions which can be distinguished by the procedures according to the invention. CRP, sTfR, and ferritin were determined via homogenous immunoassays (Tina-quaint®, Roche Diagnostics), homocysteine via a homogenous immunoassay by the company Axis Shields (Oslo, Norway) and hepcidin via an ELISA test (Hepcidin Prohormone ELISA test available from DRG, located in Marburg, Germany.)

EXAMPLES

Example 1

The markers CRP, sTfR, ferritin, hepcidin, and homocysteine of patients A to H showing the conditions given in FIG. 3 under "Commentary" were determined. The values obtained are shown in FIG. 3.

Example 2

The markers hepcidin, CRP, sTfR, and ferritin of 283 patients with inflammatory chronic diseases were determined. The results are shown in Table 1.

TABLE 1

Hepcidin-Prohormone, a new marker in Diagnosis of Disorders of Iron Metabolism

| Group | Age (years) | n | Hepcidin* (μg/L) | CRP (mg/L) | sTfR (mg/L) | Ferritin (μg/L) |
|---|---|---|---|---|---|---|
| Females | 50-50 | 48 | 141 | 1.7 | 3.2 | 70 |
|  | 60-69 | 64 | 125 | 1.7 | 3.2 | 90 |
|  | 70-80 | 28 | 121 | 2.0 | 3.2 | 89 |
| Hormone therapy |  | 37 | 123 | 1.8 | 2.8 | 94 |
| No hormone therapy |  | 105 | 136 | 1.9 | 3.3 | 77 |
| Males | 50-59 | 56 | 140 | 1.4 | 3.0 | 166 |
|  | 60-69 | 60 | 139 | 1.5 | 3.3 | 188 |
|  | 70-80 | 28 | 138 | 2.2 | 3.3 | 198 |

*Expected normal range of Hepcidin: <100-300 μg/L

The results show that hepcidin is a marker of the amount of circulating iron. If the amount of circulating iron is too high (sTfR <4 mg/l, ferritin >100 μg/l), hepcidin is released (>300 μg/l). If the amount of circulating iron is too low (sTfR >4 mg/l, ferritin <30 μg/l), hepcidin expression is stopped.

The following threshold values were found:

| | |
|---|---|
| Hepcidin, expected normal range: | <100-300 μg/L |
| sTfR/log Ferritin for patients with iron deficiency (w, m) | 0.9 |
| sTfR/log Ferritin for patients with iron overload (w, m) | 3.7 and 3.4 |
| sTfR for patients with iron deficiency (w, m) | 4.4 and 5 mg/L |
| Ferritin for patients with iron deficiency (w, m) | 15 and 30 μg/L |
| Ferritin for patients with iron overload (w, m) | 150 and 400 μg/L |
| CRP for patients with persistent acute phase reaction | >5 mg/L |

We claim:

1. A diagnostic method, comprising determining a concentration of hepcidin in a bodily fluid sample from a subject suspected of having a disorder selected from the group consisting of an inflammatory chronic disease and a non-inflammatory chronic disease, wherein an increase in hepcidin concentration in the bodily fluid sample relative to a threshold hepcidin concentration indicates an inflammatory chronic disease in the subject and distinguishes the disorder from a non-inflammatory chronic disease, and wherein lack of an increase in hepcidin concentration in the bodily fluid sample relative to a threshold concentration indicates an inflammatory chronic disease is not present in the subject , and further comprising determining a concentration of homocysteine in a bodily fluid sample from the subject, wherein an increase in homocysteine concentration in the bodily fluid sample relative to a threshold homocysteine concentration indicates a non-inflammatory chronic disease in the subject, and wherein lack of an increase in homocysteine concentration in the bodily fluid sample relative to a threshold homocysteine concentration indicates a non-inflammatory chronic disease is not present in the subject.

2. A diagnostic method, comprising determining a concentration of hepcidin in a bodily fluid sample from a subiect suspected of having a disorder selected from the group consisting of an inflammatory chronic disease, a non-inflammatory chronic disease and an acute phase reaction, wherein an increase in hepcidin concentration in the bodily fluid sample relative to a threshold hepcidin concentration indicates an inflammatory chronic disease in the subiect and distinguishes the disorder from a non-inflammatory chronic disease, and wherein lack of an increase in hepcidin concentration in the bodily fluid sample relative to a threshold hepcidin concentration indicates an inflammatory chronic disease is not present in the subiect, and further comprising determining a concentration of homocysteine in a bodily fluid sample from the subiect, wherein an increase in homocysteine concentration in the bodily fluid sample relative to a threshold homocysteine concentration indicates a non-inflammatory chronic disease in the subiect, and wherein lack of an increase in homocysteine concentration in the bodily fluid sample relative to a threshold homocysteine concentration indicates an non-inflammatory chronic disease is not present in the subiect, and determining a concentration of C-reactive protein in a bodily fluid sample from the subject, wherein an increase in C-reactive protein concentration in the bodily fluid sample relative to a threshold C-reactive protein concentration indicates an acute phase reaction in the subject, and wherein lack of an increase in C-reactive protein concentration in the bodily fluid sample relative to a threshold C-reactive protein concentration indicates an acute phase reaction is not present in the subject.

3. The method of claim 1 further comprising determining a concentration in the bodily fluid sample of one or more markers selected from the group consisting of holotranscobalamin II, methylmalonic acid, cystathionine, C-reactive protein, transferrin, soluble transferrin receptor (sTfR), ferritin, creatinine, haemoglobin, blood glucose, triglycerides, cholesterol, zinc, protoporphyrin, myoglobin, haemosiderin, catalase, peroxidase cytochrome, serum amyloid A (SAA), $\alpha_1$-antichymotrypsin, acidic $\alpha_1$ glycoprotein, $\alpha_1$ antitrypsin, haptoglobin, fibrinogen, complement component C3, complement component C4, coeruloplasmin, interleukin 6 (IL-6), leukaemia-inhibiting factor (LIF), oncostatin M, interleukin 11 (IL-11), ciliary neurotropic factor (CNTF), interleukin 160 (IL-1$\alpha$), interleukin 1$\beta$ (IL-1$\beta$), tumour necrosis factor $\alpha$ (TNF$\alpha$), tumour necrosis factor $\beta$ (TNF$\beta$), insulin, fibroblast growth factor (FGF; fibroblast growth factor), hepatocyte growth factor, transgrowth factor $\beta$ (TGF$\beta$), and interferon.

4. The method of claim 2 further comprising determining a concentration in the bodily fluid sample of one or more markers selected from the group consisting of holotranscobalamin II, methylmalonic acid, cystathionine, transferrin, soluble transferrin receptor (sTfR), ferritin, creatinine, haemoglobin, blood glucose, triglycerides, cholesterol, zinc, protoporphyrin, myoglobin, haemosiderin, catalase, peroxidase cytochrome, serum amyloid A (SAA), a$\alpha_1$-antichymotrypsin, acidic $\alpha_1$ glycoprotein, $\alpha_1$ antitrypsin, haptoglobin, fibrinogen, complement component C3, complement component C4, coeruloplasmin, interleukin 6 (IL-6), leukaemia-inhibiting factor (LIF), oncostatin M, interleukin 11 (IL-11), ciliary neurotropic factor (CNTF), interleukin 1$\alpha$ (IL-1$\alpha$), interleukin 1$\beta$ (IL-1$\beta$), tumour necrosis factor $\alpha$ (TNF$\alpha$), tumour necrosis factor $\beta$ (TNF$\beta$), insulin, fibroblast growth factor (FGF; fibroblast growth factor), hepatocyte growth factor, transgrowth factor $\beta$ (TGF$\beta$), and interferon.

5. The method of claim 1 wherein the non-inflammatory chronic condition is selected from the group consisting of vitamin B6 deficiency, vitamin B12 deficiency, folate deficiency, pellagra, funicular myelosis, pseudoencephalitis, Alzheimer's disease, coronary heart disease, and peripheral occlusive arterial disease.

6. The method of claim 2 wherein the acute phase reaction is selected from the group consisting of pancreatitis, hepatitis, and rheumatoid diseases.

7. The method of any one of claims 1,2,3,4,5, or 6 wherein the bodily fluid sample is selected from the group consisting of serum, plasma, and urine.

8. The method of any one of claims 1,2,3,4,5, or 6 wherein the threshold hepcidin concentration is between 200 and 260 ng/ml.

9. The method of any one of claims 1,2,3,4,5, or 6 wherein the threshold homocysteine concentration is between 12 and 15 µmol/l.

10. The method of any one of claims 2,3,4, or 6 wherein the threshold C-reactive protein concentration is between 9 and 11 mg/L.

* * * * *

SEQUENCE LISTING

<160> NUMBER OF SEQ ID NOS: 3

<210> SEQ ID NO 1
<211> LENGTH: 20
<212> TYPE: PRT
<213> ORGANISM: Homo sapiens

<400> SEQUENCE: 1

Ile Cys Ile Phe Cys Cys Gly Cys Cys His Arg Ser Lys Cys Gly Met
1               5                   10                  15

Cys Cys Lys Thr
            20

<210> SEQ ID NO 2
<211> LENGTH: 22
<212> TYPE: PRT
<213> ORGANISM: Homo sapiens

<400> SEQUENCE: 2

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 3
<211> LENGTH: 25
<212> TYPE: PRT
<213> ORGANISM: Homo sapiens

<400> SEQUENCE: 3

Asp Thr His Phe Pro Ile Cys Ile Phe Cys Cys Gly Cys Cys His Arg
1               5                   10                  15

Ser Lys Cys Gly Met Cys Cys Lys Thr
            20                  25